United States Patent
Ikeura et al.

(10) Patent No.: US 7,153,522 B1
(45) Date of Patent: Dec. 26, 2006

(54) SORBEFACIENTS AND PREPARATIONS FOR PERCUTANEOUS ABSORPTION CONTAINING THE SAME

(75) Inventors: Yasuhiro Ikeura, Tosu (JP); Masayoshi Maki, Tosu (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 09/807,337

(22) PCT Filed: Oct. 14, 1999

(86) PCT No.: PCT/JP99/05670

§ 371 (c)(1),
(2), (4) Date: Apr. 10, 2001

(87) PCT Pub. No.: WO00/21566

PCT Pub. Date: Apr. 20, 2000

(30) Foreign Application Priority Data

Oct. 14, 1998 (JP) .................... 10-291851

(51) Int. Cl.
*A61M 37/00* (2006.01)
*A61K 9/10* (2006.01)
*A61K 47/32* (2006.01)
*A61K 47/10* (2006.01)

(52) U.S. Cl. ................ 424/449; 424/448; 424/486

(58) Field of Classification Search ........ 424/448–449, 424/486
See application file for complete search history.

(56) References Cited

U.S. PATENT DOCUMENTS

| 4,435,180 | A | * | 3/1984 | Leeper |
| 4,820,525 | A | * | 4/1989 | Leonard et al. |
| 5,240,932 | A | * | 8/1993 | Morimoto et al. |
| 5,332,576 | A | * | 7/1994 | Mantelle |
| 5,912,008 | A | * | 6/1999 | Horstmann et al. |

FOREIGN PATENT DOCUMENTS

| EP | 0 480 054 A1 | 4/1992 |
| EP | 0 607 434 A1 | 7/1994 |
| EP | 0 622 075 A1 | 11/1994 |

* cited by examiner

*Primary Examiner*—Edward J. Webman
(74) *Attorney, Agent, or Firm*—Edwards Angell Palmer & Dodge LLP; Peter F. Corless; Mark D. Russett

(57) ABSTRACT

Percutaneous sorbefacients comprising hexylene glycol and 1-menthol, more particularly, percutaneous sorbefacients for female hormones or derivatives thereof; and preparations for percutaneous absorption which comprise a styrene/isoprene/styrene block copolymer and/or polyisobutylene, a softener and a tackifier as the base components, hormones, in particular, follicle hormone and/or luteal hormone as the drug component and hexylene glycol and 1-menthol as a sorbefacient.

5 Claims, No Drawings

SORBEFACIENTS AND PREPARATIONS FOR PERCUTANEOUS ABSORPTION CONTAINING THE SAME

TECHNICAL FIELD

The present invention relates to the field of a percutaneous drug therapy and relates to a preparation for percutaneous absorption containing hexylene glycol and 1-menthol as sorbefacients. More particularly, it relates to a preparation for percutaneous absorption which is characterized in using a styrene-isoprene-styrene block copolymer, a softener and a tackifier as a base component and hexylene glycol and 1-menthol as sorbefacients whereby permeation of a pharmaceutical agent through skin is made better and a predetermined amount of a pharmaceutical agent can be precisely and surely applied to a patient.

BACKGROUND ART

Estradiol contained in follicular hormones is secreted from ovary when females are in a reproducible period. Therefore, females around the stage of perimenopause are deficient mostly in estradiol and suffer from climacteric changes and menopausal disorder. In order to improve those symptoms, a therapy by orally administering agents is carried out at present but, since they are quickly metabolized and inactivated by digestive organs such as stomach and intestine, liver, etc., it is necessary to take high doses of estradiol for expecting a sufficient expression of the pharmaceutical effect. In addition, there is a risk of an increase in expression of adverse actions and the like due to the high doses.

Under such circumstances, there has been attempts where a therapy is carried out in which estradiol is made to reach the blood by making its metabolism little by means of a percutaneous administration. On the other hand, there have been other attempts where another hormone—luteinizing hormone—is absorbed percutaneously whereby the adverse action in the administration of estradiol is suppressed. In Japanese Patent Laid-Open No. 342532/1992, there is proposed a percutaneously absorbing preparation mainly comprising estradiol and luteinizing hormone as pharmaceutical ingredients and an acrylate adhesive consisting of 2-ethylhexyl acrylate and N-vinyl-2-pyrrolidone as an adhesive. However, an acrylate adhesive has a low releasing ability of pharmaceuticals and has a strong irritation to skin and, therefore, it is hardly durable for a continuous administration during a long period.

In Japanese Patent Laid-Open No. 51623/1994, there is proposed a method where the pharmaceutical ingredients—estradiol and norethisterone acetate—are dissolved in a gel comprising hydroxypropyl cellulose and ethanol to make them into a reservoir type and release of the pharmaceutical ingredients is controlled using a permeability adjusting membrane. However, ethanol has a strong irritation to skin and there is a problem such as an adverse action causing a flare at the applied area in a high frequency. On the other hand, a percutaneous patch comprising a styrene-isoprene-styrene block copolymer using crotamiton as a solubilizer is proposed in International Patent Laid-Open WO 91/17752 and Japanese Patent Laid-Open No. 148145/1993. However, there is a problem in its stability that, when crotamiton is used as a solubilizer, the styrene-isoprene-styrene block copolymer itself is dissolved in crotamiton whereby the expected cohesive force is not achieved.

Hexylene glycol (generic name; its chemical name is 2-methyl-2,4-pentanediol) is usually used as moisturizer, solvent, cleaning agent in industry, hydraulic fluid, softener/softening agent for leather fiber, etc., agent for ink, agent for photography and the like. In Japanese Patent Laid-Open Nos. 109220/1995 and 53338/1996, there are proposed the agents for external use where hexylene glycol is used as an antibacterial agent. In International Patent Laid-Open WO 96/19976 and Japanese Patent Laid-Open No. 138153/1995, there are proposed the agents for external use where hexylene glycol is used as a sorbefacient. However, hexylene glycol has a high compatibility with acrylate bases and, in achieving a sufficient sorbefacient effect, it is necessary to compound hexylene glycol in a large amount. There is an additional problem of lowering of adhesive property and influence on the basic physical property of the preparation caused by compounding of a large quantity of hexylene glycol.

In view of the above problems, the present inventors have carried out an intensive investigation with an object of providing a percutaneous preparation or base in which 1) a high cutaneous permeation of pharmaceutical ingredients and 2) stabilization of physical property of the base are attempted and, as a result, the present invention has been accomplished.

DISCLOSURE OF THE INVENTION

As a result of an intensive investigation for solving the above-mentioned problems, the present inventors have found that a combination of hexylene glycol (chemical name: 2-methyl-2,4-pentanediol) and 1-menthol has a high percutaneous sorbefacient action. More particularly, they have found that hexylene glycol and 1-menthol have an excellent percutaneously sorbefacient action to female hormones and derivatives thereof such as follicular hormone, luteinizing hormone and derivatives thereof. Thus, the present invention relates to a sorbefacient comprising hexylene glycol and 1-menthol or, preferably, to a percutaneously sorbefacient for female hormones or derivatives thereof.

The present invention further relates to a percutaneous base containing a base component for percutaneous absorption and hexylene glycol and 1-menthol having sufficient amounts for achieving a percutaneously sorbefacient action. With regard to the base component for percutaneous absorption, that which contains a styrene-isoprene-styrene block copolymer and/or polyisobutylene, softener and tackifier is preferred.

To be more particularly, it has been found that a percutaneously absorbing preparation having good cohesive property, stabilized physical property of the preparation and good skin permeation of the pharmaceutical agent can be prepared by the use of a styrene-isoprene-styrene block copolymer and/or polyisobutylene, softener, tackifier, hexylene glycol and 1-menthol as a base component whereupon the present invention has been achieved.

The present invention relates to a base for a percutaneously absorbing patch containing a styrene-isoprene-styrene block copolymer and/or polyisobutylene, softener, tackifier, hexylene glycol and 1-menthol as a base component and also to a percutaneously absorbing patch containing the said base for a percutaneously absorbing patch and pharmaceuticals.

BEST MODE FOR CARRYING OUT THE INVENTION

It is necessary that the pharmaceutical agent which is an effective ingredient of the percutaneously absorbing preparation of the present invention is a physiologically active substance and has a percutaneously absorbing ability. Alternatively, the agent may be the so-called prodrug which shows a physiological action after being percutaneously absorbed. The agent includes a pharmaceutical acceptable inorganic or organic addition salt as well.

With regard to the pharmaceutical agent for the percutaneously absorbing preparation of the present invention, female hormones such as follicular hormone, luteinizing hormone and derivatives thereof are preferably exemplified. For example, follicular hormone such as estradiol, estrone, estriol, equilin, equilenin and derivatives thereof may listed as an active ingredient and, preferably, estradiol is mostly used in the percutaneously absorbing preparation of the present invention. With regard to the luteinizing hormone, progesterone, hydroxyprogesterone caproate, hydroxyprogesterone acetate, dydrogesterone, chlormadinone acetate, ethisterone, dimethisterone, norethisterone, norethisterone acetate, norethisterone enanthate, ethynodiol acetate, megestrol acetate and allylestrenol are exemplified and, preferably, norethisterone and norethisterone acetate are mostly used for the percutaneously absorbing preparation of the present invention.

Besides the above, examples of the pharmaceutical agent which is effective and able to be used for the percutaneously absorbing preparation of the present invention are antiemetic agents (such as granisetron hydrochloride, azasetron hydrochloride, ondansetron hydrochloride and ramosetron hydrochloride), remedies for pollakiuria (such as oxybutynin hydrochloride), calcium antagonists (such as nifedipine, nisoldipine, nicardipine and nitrendipine), corticosteroid substances (such as hydrocortisone, prednisolone and clobetasol propionate), anti-inflammatory/analgesic agents (such as indomethacin, ketoprofen, flurbiprofen, felbinac and ketorolac), hypnotic/sedative agents (such as phenobarbital, triazolam, nitrazepam and lorazepam), tranquilizers (such as fluphenazine, diazepam and chlorpromazine), antihypertensive agents (such as clonidine, clonidine hydrochloride, pindolol, propranolol, nitrendipine and metoprolol), hypotensive diuretic agents (such as hydrothiazide), antibiotic substances (such as penicillin, tetracycline, erythromycin and chloramphenicol), anesthetic agents (such as lidocaine, dibucaine hydrochloride and ethyl aminobenzoate), antibacterial substances (such as benzalkonium hydrochloride and clotrimazole), vitamins (such as vitamin A), antiepileptic agents (such as nitrazepam), coronary vasodilators (such as nitroglycerine and isosorbide nitrate), antihistaminic agents (such as diphenhydramine and chlorpheniramine), antitussive agents (such as tulobuterol hydrochloride, salbutamol, ketotifen fumarate, tranilast and isoproterenol hydrochloride), antidepressants (such as clomipramine hydrochloride and amitriptyline hydrochloride), cerebral circulation improving agents (such as dihydroergotoxine mesylate and ifenprodil), anti-tumor agents (such as 5-fluorouracil), muscle relaxants (such as eperisone and dantrolene), analgesics (such as fentanyl and morphine), hormone preparations of a polypeptide type (luteinizing hormone-releasing hormone [LH-RH] and thyrotropin-releasing hormone [TRH]), peripheral blood vessel dilators, immunomodulators (such as polysaccharides, auranofin and lobenzarit), cholagogues (such as ursodeoxycholic acid), diuretics (such as hydroflumethiazide), agents for diabetes mellitus (such as tolbutamide), remedies for gout (such as colchicine), anti-parkinsonian agents (such as amantadine and levodopa) and anti-dizziness agents (such as difenidol and betahistine) and, although the compounding amount thereof effective for the therapy is different for the object of compounding, it is usually preferred to be 0.1–10% by weight to the preparation. When those pharmaceuticals do not cause inconvenience by their interaction, two or more of them may be jointly used upon necessity.

According to the combination of a styrene-isoprene-styrene block copolymer and/or polyisobutylene, softener, tackifier, hexylene glycol and 1-menthol in the percutaneously absorbing base of the present invention, a high release of pharmaceuticals which has not been achieved by the conventional single acrylate base is now possible and, in addition, a high permeation through the skin is available.

Further, hexylene glycol can be used within such a range that the base component, particularly a styrene-isoprene-styrene block copolymer and/or polyisobutylene, is not substantially dissolved therein or its substantial dissolving therein is not observed while 1-menthol can be also used within such a range that it does not affect a physical property and, accordingly, good tackiness and stability can be achieved.

Contents of those essential components in the total amount of the preparation are as follows.

Thus, 10–40% by weight, preferably 15–30% by weight or, more preferably, 17–23% by weight for a styrene-isoprene-styrene block copolymer; 2–10% by weight, preferably 2.5–7% by weight or, more preferably, 3–5% by weight for polyisobutylene; 10–60% by weight, preferably 12–55% by weight or, more preferably, 15–50% by weight for a softener; 20–60% by weight, preferably 23–57% by weight or, more preferably, 25–50% by weight of a tackifier; and a combination within such a range affords the best advantage of the present invention.

When the amount of the styrene-isoprene-styrene block copolymer and/or polyisobutylene is less than the above range, a cohesive force is insufficient while, when it is more than that, softness of the preparation is little resulting in a problem in terms of stickiness. When the amount of the softener is less than the above range, softness of the preparation is little resulting in a problem in terms of stickiness while, when it is more than that, softness becomes big but there is a problem in terms of cohesive force of the preparation. The tackifier has a compatibility with hexylene glycol and 1-menthol. When the amount of the tackifier is little, a sufficient compounding of hexylene glycol with 1-menthol is not possible and a sufficient sorbefacient effect by hexylene glycol and 1-menthol is not achieved.

Hexylene glycol which is one of the components of the present invention has been known to be used as a moisturizer and an antibacterial agent as a cosmetic material. However, in the present invention, a sufficient amount thereof is to be compounded as a sorbefacient for the pharmaceutical component and the compounding amount is 1–10% by weight, preferably 1.5–8% by weight or, more preferably, 2–7% by weight. When the compounding amount is less than 1% by weight, stabilizing and sorbefacient effects for the physical property of the base are insufficient while, when it is more than 10% by weight, a bleeding by hexylene glycol is resulted.

With regard to 1-menthol which is used as a sorbefacient together with hexylene glycol, its sorbefacient effect has been confirmed already but it results in a synergistic effect when combined with hexylene glycol. Its compounding amount is 0.1–7% by weight, preferably 0.5–6% by weight or, more preferably, 1–5% by weight. When the compounding amount is less than 0.1% by weight, a sorbefacient effect is insufficient while, when it is more than 7% by weight, cohesive force of the base components lowers.

With regard to the compounding ratio of hexylene glycol to 1-menthol, when the ratio in terms of (hexylene glycol):(1-menthol) is 1:0.1 or less, an sorbefacient effect for the pharmaceutical agent is little while, when it is 1:7 or more, hexylene glycol bleeds and cohesive force of the patch lowers. In the present invention, an advantage is achieved when the ratio of hexylene glycol to 1-menthol is within a range of from 1:0.1 to 1:7 and, more preferably, when it is from 2:1 to 7:5, the highest sorbefacient effect is achieved and the physical property becomes good as well.

With regard to the dosage form of the percutaneously absorbing patch of the present invention, plaster is most preferred and an anhydrous plaster containing substantially no water is particularly preferred.

Examples of the styrene-isoprene-styrene block copolymer are styrene-isoprene-styrene block copolymers manufactured by Shell Chemical (trade names: Cariflex TR-1107 and Cariflex TR-1111), styrene-isoprene-styrene block copolymers manufactured by Nippon Synthetic Rubber (trade names: JSR 5000 and JSR 5100) and a styrene-isoprene-styrene block copolymer manufactured by Nippon Zeon (trade name: Quintac 3421).

Examples of polyisobutylene are polyisobutylene manufactured by Exxon (trade name: Vistanex) and polyisobutylene manufactured by BASF (trade name: Opanol).

Examples of the softener are liquid paraffin, polybutene, castor oil, cotton seed oil, palm oil, coconut oil and process oil.

Examples of the tackifier are alicyclic saturated hydrocarbon resins (such as Arkon P-100 [trade name]), rosin esters (such as KE-311 and KE-100 [trade names] and Super Ester S-100 [trade name]), hydrogenated alicyclic hydrocarbons (such as Escorez 5300 [trade name]), hydrogenated resins of a terpene type (such as Clearon P-105 [trade name]), hydrogenated rosin esters (such as Foral 105 [trade name]) and modified rosin esters modified with dibasic acid (such as Pentalyn 4741 [trade name]). Those tackifiers may be used by mixing two or more of them upon necessity.

It is necessary that a film which is to be a support of the present invention has a property of, for example, excellent so-called barrier property for the prevention of leakage, evaporation and adsorption of the pharmaceutical agent. In addition, it preferably has an appropriate softness when an apparatus is applied to the skin. With regard to a material for the support, there is no particular limitation so far as it has the above-mentioned conditions and its specific examples are aluminum, ethylene-vinyl acetate copolymer or a saponified product thereof, cellulose acetate, cellulose, Nylon, polyester, polyethylene, polyvinylidene chloride, polycarbonate, polyvinyl alcohol and polypropylene. Those materials may be made into film, made into a layered film by laminating after making into a form of paper or cloth if necessary or subjected to a treatment such as aluminum evaporation or ceramic evaporation whereupon a barrier property is improved.

With regard to a film which is to be a detachable liner layer, the film is necessary to prevent its leakage and evaporation from the pharmaceutical agent layer during the storage of the apparatus and, in addition, the detachable liner layer should be able to be detached upon the use of the apparatus. With regard to the material for the detachable liner film which can be used, its specific examples are aluminum, cellulose, polyester, polyethylene and polypropylene and, if necessary, such a film may be layered. Alternatively, its surface may be treated with silicon, fluorocarbon or the like or a known additive may be compounded with a liner material so that the detaching property is adjusted or a barrier property is adjusted. In the detachable liner, there may be provided a knob for the detachment so that a handling upon detachment becomes easy.

Further, with an object of adjustment of adhesive property, safety and stability, known additives may be compounded if necessary. Specific examples thereof are water-absorbing polymers such as Sumikagel SP-520 (trade name), Aquakeep 10SH (trade name), Arasorb 800F (trade name) and Sanwet 1M-1000MPS (trade name); inorganic fillers such as zinc oxide, calcium carbonate, titanium dioxide and silica substances; solubilizing aids such as glycerol fatty acid ester (e.g., Excel [trade name]) and crotamiton; other sorbefacients such as aliphatic alcohol (e.g., Kalcohl [trade name]); and moisturizers such as triethyl citrate, polyethylene glycol and glycerol. They may be appropriately contained in appropriate amounts.

Now a method for the manufacture of the percutaneously absorbing preparation of the present invention will be illustrated as hereunder. The percutaneously absorbing preparation of the present invention may be manufactured in such a manner, for example, that all base components except pharmaceutical ingredient, hexylene glycol and 1-menthol are dissolved by heating, then pharmaceutical ingredient, hexylene glycol and 1-menthol are added thereto and mixed therewith and, after the mixture is spread on the above-mentioned support if necessary, it is covered with a liner followed by cutting into a desired shape to give a product or that the mixture is once spread on a film which is subjected to a detachable treatment and then transferred onto an appropriate support with pressure to give a product. It is also possible that all components are dissolved in an organic solvent such as hexane, toluene or ethyl acetate, the solution is spread on the above-mentioned support, the organic solvent is removed therefrom and the residue is covered by a liner followed by cutting into a desired shape to give a product or that, after once spreading on a film which is subjected to a detachable treatment and the organic solvent is removed therefrom followed by transferring to an appropriate support by compressing to give a product.

EXAMPLES

The percutaneously absorbing patch of the present invention will now be illustrated in more detail by way of Examples and Test Examples as hereunder although the present invention is not limited to those examples. Incidentally, all numerals in Examples, Comparative Examples and Referential Examples are those % by weight.

EXAMPLE 1

| | |
|---|---|
| Styrene-isoprene-styrene block copolymer | 10 |
| Liquid paraffin | 60 |
| Tackifier (alicyclic saturated hydrocarbon resin; trade name: Arkon P-100) | 20 |
| Polyisobutylene | 7.3 |
| Hexylene glycol | 1 |
| 1-Menthol | 0.1 |
| Dibutylhydroxytoluene | 1 |
| Estradiol | 0.1 |
| Norethisterone | 0.5 |

The manufacturing method mentioned above was carried out according to this formulation followed by cutting into a desired size to give a mixed preparation of estradiol and norethisterone.

EXAMPLE 2

| | |
|---|---|
| Styrene-isoprene-styrene block copolymer | 40 |
| Liquid paraffin | 10 |
| Tackifier (rosin ester; trade name: KE-311) | 15 |
| Polyisobutylene | 2 |
| Hexylene glycol | 10 |
| l-Menthol | 7 |
| Dibutylhydroxytoluene | 1 |
| Estradiol | 5 |
| Norethisterone acetate | 10 |

The manufacturing method mentioned above was carried out according to this formulation followed by cutting into a desired size to give a mixed preparation of estradiol and norethisterone acetate.

EXAMPLE 3

| | |
|---|---|
| Styrene-isoprene-styrene block copolymer | 19.5 |
| Liquid paraffin | 15 |
| Tackifier (hydrogenated rosin ester; trade name: Foral 105) | 60 |
| Hexylene glycol | 1 |
| l-Menthol | 0.5 |
| Dibutylhydroxytoluene | 1 |
| Estradiol | 1 |
| Norethisterone acetate | 2 |

The manufacturing method mentioned above was carried out according to this formulation followed by cutting into a desired size to give a mixed preparation of estradiol and norethisterone acetate.

EXAMPLE 4

| | |
|---|---|
| Styrene-isoprene-styrene block copolymer | 20 |
| Liquid paraffin | 35.4 |
| Tackifier (hydrogenated rosin ester; trade name: Foral 105) | 30 |
| Polyisobutylene | 8.6 |
| Hexylene glycol | 2 |
| l-Menthol | 1 |
| Estradiol | 1 |
| Norethisterone acetate | 2 |

The manufacturing method mentioned above was carried out according to this formulation followed by cutting into a desired size to give a mixed preparation of estradiol and norethisterone acetate.

EXAMPLE 5

| | |
|---|---|
| Styrene-isoprene-styrene block copolymer | 20 |
| Liquid paraffin | 28 |
| Tackifier (hydrogenated rosin ester; trade name: Foral 105) | 30 |
| Polyisobutylene | 10 |
| Hexylene glycol | 7 |
| l-Menthol | 1 |
| Dibutylhydroxytoluene | 1 |
| Estradiol | 1 |
| Norethisterone acetate | 2 |

The manufacturing method mentioned above was carried out according to this formulation followed by cutting into a desired size to give a mixed preparation of estradiol and norethisterone acetate.

EXAMPLE 6

| | |
|---|---|
| Styrene-isoprene-styrene block copolymer | 20 |
| Liquid paraffin | 31 |
| Tackifier (hydrogenated rosin ester; trade name: Foral 105) | 30 |
| Polyisobutylene | 5 |
| Hexylene glycol | 7 |
| l-Menthol | 3 |
| Dibutylhydroxytoluene | 1 |
| Estradiol | 1 |
| Norethisterone acetate | 2 |

The manufacturing method mentioned above was carried out according to this formulation followed by cutting into a desired size to give a mixed preparation of estradiol and norethisterone acetate.

EXAMPLE 7

| | |
|---|---|
| Styrene-isoprene-styrene block copolymer | 23 |
| Liquid paraffin | 31 |
| Tackifier (hydrogenated rosin ester; trade name: Foral 105) | 30 |
| Polyisobutylene | 4 |
| Hexylene glycol | 1 |
| l-Menthol | 7 |
| Dibutylhydroxytoluene | 1 |
| Estradiol | 1 |
| Norethisterone acetate | 2 |

The manufacturing method mentioned above was carried out according to this formulation followed by cutting into a desired size to give a mixed preparation of estradiol and norethisterone acetate.

EXAMPLE 8

| | |
|---|---|
| Styrene-isoprene-styrene block copolymer | 23 |
| Liquid paraffin | 19.9 |
| Tackifier (hydrogenated rosin ester; trade name: Foral 105) | 40 |
| Polyisobutylene | 3 |
| Hexylene glycol | 10 |
| l-Menthol | 0.1 |
| Dibutylhydroxytoluene | 1 |
| Estradiol | 1 |
| Norethisterone acetate | 2 |

The manufacturing method mentioned above was carried out according to this formulation followed by cutting into a desired size to give a mixed preparation of estradiol and norethisterone acetate.

EXAMPLE 9

| | |
|---|---|
| Styrene-isoprene-styrene block copolymer | 17 |
| Liquid paraffin | 44 |
| Tackifier (hydrogenated rosin ester; trade name: Foral 105) | 25 |
| Polyisobutylene | 4 |
| Hexylene glycol | 3 |
| l-Menthol | 3 |
| Dibutylhydroxytoluene | 1 |
| Estradiol | 1 |
| Norethisterone acetate | 2 |

The manufacturing method mentioned above was carried out according to this formulation followed by cutting into a desired size to give a mixed preparation of estradiol and norethisterone acetate.

EXAMPLE 10

| | |
|---|---|
| Styrene-isoprene-styrene block copolymer | 20 |
| Liquid paraffin | 35 |
| Tackifier (hydrogenated rosin ester; trade name: Foral 105) | 30 |
| Polyisobutylene | 5 |
| Hexylene glycol | 2 |
| l-Menthol | 4 |
| Dibutylhydroxytoluene | 1 |
| Estradiol | 1 |
| Norethisterone acetate | 2 |

The manufacturing method mentioned above was carried out according to this formulation followed by cutting into a desired size to give a mixed preparation of estradiol and norethisterone acetate.

EXAMPLE 11

| | |
|---|---|
| Styrene-isoprene-styrene block copolymer | 18 |
| Liquid paraffin | 30 |
| Tackifier (hydrogenated rosin ester; trade name: Foral 105) | 34 |
| Polyisobutylene | 4 |
| Hexylene glycol | 6 |
| l-Menthol | 4 |
| Dibutylhydroxytoluene | 1 |
| Estradiol | 1 |
| Norethisterone acetate | 2 |

The manufacturing method mentioned above was carried out according to this formulation followed by cutting into a desired size to give a mixed preparation of estradiol and norethisterone acetate.

EXAMPLE 12

| | |
|---|---|
| Styrene-isoprene-styrene block copolymer | 20 |
| Liquid paraffin | 26 |
| Tackifier (hydrogenated rosin ester; trade name: Foral 105) | 30 |
| Polyisobutylene | 10 |
| Hexylene glycol | 7 |
| l-Menthol | 3 |
| Dibutylhydroxytoluene | 1 |
| Ketoprofen | 3 |

The manufacturing method mentioned above was carried out according to this formulation followed by cutting into a desired size to give a preparation of ketoprofen.

EXAMPLE 13

| | |
|---|---|
| Styrene-isoprene-styrene block copolymer | 20 |
| Liquid paraffin | 26 |
| Tackifier (hydrogenated rosin ester; trade name: Foral 105) | 30 |
| Polyisobutylene | 10 |
| Hexylene glycol | 7 |
| l-Menthol | 3 |
| Dibutylhydroxytoluene | 1 |
| Oxybutynin | 3 |

The manufacturing method mentioned above was carried out according to this formulation followed by cutting into a desired size to give a preparation of oxybutynin.

EXAMPLE 14

| | |
|---|---|
| Styrene-isoprene-styrene block copolymer | 20 |
| Liquid paraffin | 26 |
| Tackifier (hydrogenated rosin ester; trade name Foral 105) | 30 |
| Polyisobutylene | 10 |
| Hexylene glycol | 7 |
| l-Menthol | 3 |
| Dibutylhydroxytoluene | 1 |
| Fentanyl citrate | 3 |

The manufacturing method mentioned above was carried out according to this formulation followed by cutting into a desired size to give a preparation of fentanyl citrate.

Comparative Example 1

No Hexyl Glycol Compounded

| | |
|---|---|
| Styrene-isoprene-styrene block copolymer | 20 |
| Liquid paraffin | 31 |
| Tackifier (hydrogenated rosin ester; trade name: Foral 105) | 30 |
| Polyisobutylene | 5 |
| l-Menthol | 10 |
| Dibutylhydroxytoluene | 1 |
| Estradiol | 1 |
| Norethisterone acetate | 2 |

The manufacturing method mentioned above was carried out according to this formulation followed by cutting into a desired size to give a mixed preparation of estradiol and norethisterone acetate.

Comparative Example 2

No 1-Menthol Compounded

| | |
|---|---|
| Styrene-isoprene-styrene block copolymer | 20 |
| Liquid paraffin | 26 |
| Tackifier (hydrogenated rosin ester; trade name: Foral 105) | 30 |
| Polyisobutylene | 5 |
| Hexylene glycol | 15 |
| Dibutylhydroxytoluene | 1 |
| Estradiol | 1 |
| Norethisterone acetate | 2 |

The manufacturing method mentioned above was carried out according to this formulation followed by cutting into a desired size to give a mixed preparation of estradiol and norethisterone acetate.

Comparative Example 3

Acrylate Type Base

| | |
|---|---|
| TS-620 (manufactured by Nippon Carbide) | 94 |
| l-Menthol | 3 |
| Estradiol | 1 |
| Norethisterone acetate | 2 |

The manufacturing method mentioned above was carried out according to this formulation followed by cutting into a desired size to give a mixed preparation of estradiol and norethisterone acetate.

Comparative Example 4

Acrylate Type Base

| | |
|---|---|
| TS-620 (manufactured by Nippon Carbide) | 90 |
| Hexylene glycol | 7 |
| Estradiol | 1 |
| Norethisterone acetate | 2 |

The manufacturing method mentioned above was carried out according to this formulation followed by cutting into a desired size to give a mixed preparation of estradiol and norethisterone acetate.

Comparative Example 5

Acrylate Type Base

| | |
|---|---|
| TS-620 (manufactured by Nippon Carbide) | 87 |
| Hexylene glycol | 7 |
| l-Menthol | 3 |
| Estradiol | 1 |
| Norethisterone acetate | 2 |

The manufacturing method mentioned above was carried out according to this formulation followed by cutting into a desired size to give a mixed preparation of estradiol and norethisterone acetate.

Test Example 1

Physical Property of the Preparation

Test pieces of Examples 1, 2, 3, 6, 7, 12, 13 and 14 and those of Comparative Examples 1 and 2 were subjected to an operation that a finger was pushed to the surface of the plaster for about one second for five times on the same place and cohesive force, finger tack and bleed were evaluated from the state of the plaster at that time. The result is shown in Table 1.

TABLE 1

| | Cohesive Force | Finger Tack | Bleed |
|---|---|---|---|
| Example 1 | o | o | oo |
| Example 2 | o | o | o |
| Example 3 | oo | oo | oo |
| Example 6 | oo | oo | oo |
| Example 7 | o | o | oo |
| Example 12 | oo | oo | oo |
| Example 13 | oo | oo | oo |
| Example 14 | oo | oo | oo |
| Comparative Example 1 | x | Δ | o |
| Comparative Example 2 | Δ | x | x |

In Table 1, "oo" means "very good", "o" means "good", "Δ" means "a bit bad" and "x" means "bad". In the test pieces of the Examples, there was no problem in terms of all of cohesive force, tack and bleed while, in the test piece of Comparative Example 1, there was a problem in cohesive force and, in the test piece of Comparative Example 2, the bleed was noticed a decrease in finger tack was noted.

Test Example 2

Test on Skin Irritation

The test pieces of Examples 2, 6, 7, 12, 13 and 14 and those of Comparative Examples 1, 3, 4 and 5 were subjected to a skin irritation test by the following means. Thus, a test piece was applied onto an upper arm of each ten persons (healthy and normal males) and, after application for 24 hours, the skin irritation was evaluated. The result is shown in Table 2.

TABLE 2

|  | Skin Irritation (SI Value) |
| --- | --- |
| Example 2 | 30 |
| Example 6 | 25 |
| Example 7 | 25 |
| Example 12 | 25 |
| Example 13 | 25 |
| Example 14 | 25 |
| Comparative Example 1 | 40 |
| Comparative Example 3 | 45 |
| Comparative Example 4 | 45 |
| Comparative Example 5 | 45 |

In Comparative Examples 1, 3, 4 and 5, the result with high skin irritations was noted.

Test Example 3

Test on Skin Permeation

The test pieces of Examples 2, 6, 7 and 11 and Comparative Examples 1, 2 and 5 were subjected to a permeation test to the skin of the back (temperature: 37° C.) of hairless mice (6 weeks age; female) using a diffusion cell of a Franz type. After the start of the test, a receptor solution was collected with predetermined intervals and, immediately thereafter, a receptor solution was supplemented whereby the amount of the pharmaceuticals permeated into the receptor solution was measured by a high performance liquid chromatographic method. Sample numbers for each test piece were 3. The maximum permeation speeds of estradiol ($E_2$) and norethisterone acetate (NETA) are shown in Table 3.

TABLE 3

|  | Maximum Permeation Speed ($\mu g/cm^2/hr$) | |
| --- | --- | --- |
|  | $E_2$ | NETA |
| Example 2 | 1.3 | 1.1 |
| Example 6 | 1.2 | 1.0 |
| Example 7 | 1.1 | 0.9 |
| Example 11 | 1.2 | 1.0 |
| Comparative Example 1 | 0.5 | 0.3 |
| Comparative Example 2 | 0.5 | 0.4 |
| Comparative Example 5 | 0.4 | 0.3 |

Preparations of the Examples showed better permeation of the pharmaceuticals than those of the Comparative Examples.

INDUSTRIAL APPLICABILITY

The percutaneously absorbing preparation or, preferably, the percutaneously absorbing patch of the present invention prepared as such increases the permeation of the pharmaceutical ingredient through the skin and shows excellent effects of stable base, good cohesive property, low skin irritation and high skin permeation when hexylene glycol and 1-menthol are compounded therewith.

After the percutaneously absorbing patch of the present invention is applied to the skin of a patient, the pharmaceuticals in a therapeutically effective amount is precisely and surely absorbed from the skin.

Moreover, in the percutaneously absorbing preparation of the present invention, degree of freedom of the pharmaceutical composition is high and, accordingly, there is a big advantage in a suitable design of high skin permeation of the pharmaceutical ingredient, stability of the base and efficacy upon therapy.

The invention claimed is:

1. A base for a percutaneously absorbing preparation, comprising 10–40% by weight of styrene-isoprene-styrene block copolymer, 2–10% by weight of polyisobutylene, 10–60% by weight of softener, 20–60% by weight of tackifier, 1–10% by weight of hexylene glycol and 0.1–7% by weight of 1-menthol.

2. A percutaneously absorbing preparation wherein a pharmaceutical agent is contained as an effective ingredient in the base for a percutaneously absorbing preparation according to claim 1.

3. The percutaneously absorbing preparation according to claim 2, wherein the pharmaceutical agent is follicular hormone and/or luteinizing hormone.

4. The percutaneously absorbing preparation according to claim 3, wherein the follicular hormone is estradiol, estrone, estriol, equilin or equilenin or a derivative thereof and its compounding amount if is 0.1–5% by weight.

5. The percutaneously absorbing preparation according to claim 3, wherein the luteinizing hormone is norethisterone, norethisterone acetate, norethisterone coanthale or progesterone and its compounding amount is 0.5–10% by weight.

* * * * *